(12) United States Patent
Hoshino et al.

(10) Patent No.: US 7,432,089 B2
(45) Date of Patent: Oct. 7, 2008

(54) DNA ENCODING FAVIN-ADENINE-DINUCLEOTIDE-DEPENDENT-D-ERYTHRONATE-4-PHOSPHATE-DE-HYDROGENASE, PDXR, AND MICROBIAL PRODUCTION OF VITAMIN $B_6$

(75) Inventors: Tatsuo Hoshino, Kanagawa-ken (JP); Keiko Ichikawa, Kanagawa-ken (JP); Masaaki Tazoe, Kanagawa-ken (JP)

(73) Assignee: DSM IP Assets B.V., TE Heerlen (NL)

( * ) Notice: Subject to any disclaimer, the term of this patent is extended or adjusted under 35 U.S.C. 154(b) by 0 days.

(21) Appl. No.: 10/528,844

(22) PCT Filed: Sep. 25, 2003

(86) PCT No.: PCT/EP03/10684

§ 371 (c)(1), (2), (4) Date: Feb. 3, 2006

(87) PCT Pub. No.: WO2004/029250

PCT Pub. Date: Apr. 8, 2004

(65) Prior Publication Data

US 2006/0141590 A1    Jun. 29, 2006

(30) Foreign Application Priority Data

Sep. 27, 2002    (EP) ................... 02021641

(51) Int. Cl.
| | |
|---|---|
| C12P 17/06 | (2006.01) |
| C12P 17/12 | (2006.01) |
| C12Q 1/68 | (2006.01) |
| C12N 21/06 | (2006.01) |
| C12N 15/70 | (2006.01) |
| C12N 1/20 | (2006.01) |
| C12N 1/00 | (2006.01) |
| C12N 9/04 | (2006.01) |
| C07H 21/04 | (2006.01) |

(52) U.S. Cl. ............... 435/125; 435/122; 435/6; 435/69.1; 435/320.1; 435/252.3; 435/254.9; 435/190; 536/23.2

(58) Field of Classification Search ............. 435/125, 435/6, 69.1, 320.1, 252.3, 254.9, 190; 536/23.2
See application file for complete search history.

(56) References Cited

U.S. PATENT DOCUMENTS

2005/0164335 A1*    7/2005    Yocum et al. ............... 435/66

OTHER PUBLICATIONS

Tazoe et al. (Biosynthesis of vitamin B6 in Rhizobium: in vitro synthesis of pyridoxine from 1-deoxy-D-xylulose and 4-hydroxy-L-threonine, Biosci Biotechnol Biochem. Apr. 2002;66(4):934-6).*
Capela, D. et al. "Analysis of the Chromosome Sequence of the Legume Symbiont *Sinorhizobium meliloti* Strain 1021," *Proc. Natl. Acad. Sci.*, v. 98, No. 17, pp. 9877-9882 (2001).
Capela, D. et al. Database SWALL Database Abstract No. XP-002266688 (2001).
Pease, A.J. et al. "Positive Growth Rate-Dependent Regulation of the pdxA, ksgA, and pdxB Genes of *Escherichia coli* K-12," *J. Bacteriol.*, v. 184, No. 5, pp. 1359-1369 (2002).
EMBL- EBI Database Abstract No. XP-002266689 (2002).

* cited by examiner

*Primary Examiner*—Rebecca E. Prouty
*Assistant Examiner*—Iqbal H Chowdhury
(74) *Attorney, Agent, or Firm*—Bryan Cave LLP

(57) ABSTRACT

The present invention relates to a DNA encoding a novel flavin adenine dinucleotide (FAD)-dependent D-erythronate 4-phosphate (EN4P) dehydrogenase originated from *Sinorhizobium meliloti*, which is involved in vitamin B6 biosynthesis, and a recombinant microorganism transformed with a vector having the DNA. It also relates to a process for production of vitamin B6 by using the recombinant microorganism. "Vitamin B6" as used in this invention includes pyridoxol (PN), pyridoxal and pyridoxamine. Vitamin B6 is a vitamin indispensable to human beings or other animals, and is used as a raw material of medicines or as feed additives.

3 Claims, No Drawings

DNA ENCODING FAVIN-ADENINE-DINUCLEOTIDE-DEPENDENT-D-ERYTHRONATE-4-PHOSPHATE-DEHYDROGENASE, PDXR, AND MICROBIAL PRODUCTION OF VITAMIN $B_6$

This application is the National Stage of International Application No. PCT/EP2003/010684, filed Sep. 25, 2003.

The present invention relates to a DNA encoding a novel flavin adenine dinucleotide (FAD)-dependent D-erythronate 4-phosphate (EN4P) dehydrogenase originated from *Sinorhizobium meliloti*, which is involved in vitamin $B_6$ biosynthesis, and a recombinant microorganism transformed with a vector having the DNA. It also relates to a process for production of vitamin $B_6$ by using the recombinant microorganism.

"Vitamin $B_6$" as used in this invention includes pyridoxol (PN), pyridoxal and pyridoxamine. Vitamin $B_6$ is a vitamin indispensable to human beings or other animals, and is used as a raw material of medicines or as feed additives.

Fermentative production of vitamin $B_6$ by *Sinorhizobium* [also known as *Rhizobium*: De Lajudie et al., Int. J. Syst. Bacteriol. 44:715-733 (1994)] *meliloti* is reported (EP 765, 938). But the production efficiency of vitamin $B_6$ in the process for preparing vitamin $B_6$ using a microorganism is not so high and it has been required to construct a new microorganism having higher productivity of vitamin $B_6$.

4-PHT pathway in *E. coli* is as follows: 4-PHT synthesis starts from D-erythrose 4-phosphate (E4P), which is oxidized by an E4P dehydrogenase to EN4P, further oxidized by an EN4P dehydrogenase to 2-keto-EN4P, and transaminated by an aminotransferase to yield 4-PHT. The three enzymes, E4P dehydrogenase, EN4P dehydrogenase, and aminotransferase, are encoded by three genes, named epd, pdxB, and serC, respectively, and there is only one report on the EN4P dehydrogenase of *E. coli*, which requires $NAD^+$ as a coenzyme for the enzyme reaction [Zhao et al., J. Bacteriol. 177:2804-2812 (1995)].

On the other hand, the 4-PHT in *S. meliloti* is synthesized from glycine and glycolaldehyde. But a gene responsible to the reaction has not been identified yet. For the purpose of identifying the gene, we obtained a vitamin $B_6$-deficient mutant of *S. meliloti* IFO 14782 that is defective in 4-PHT formation. And we obtained a gene, namely pdxR, which complements the vitamin $B_6$-deficient mutant, and found that pdxR encodes a novel FAD-dependent EN4P dehydrogenase.

According to the present invention, it is possible to improve the production efficiency of vitamin $B_6$ greatly by fermentation using a microorganism of the genus *Sinorhizobium* having a recombinant plasmid comprising a vector containing pdxR. Vitamin $B_6$ can advantageously be produced in the culture broth by cultivating said microorganisms and can be recovered therefrom in a desired purity.

The present invention provides a DNA encoding an FAD-dependent EN4P dehydrogenase originating from *Sinorhizobium*; expression vectors carrying a DNA containing the DNA encoding the EN4P dehydrogenase; a transformed host cell carrying the expression vectors; a polypeptide possessing FAD-dependent EN4P dehydrogenase activity produced in the host cell; and a process for producing vitamin $B_6$ by using the host cell.

All scientific and technical terms used in this invention have meanings commonly used in the art unless otherwise specified.

The present invention is based on the discovery of a gene designated pdxR, which encodes an FAD-dependent EN4P dehydrogenase, which is involved in vitamin $B_6$ biosynthesis of *S. meliloti* and the use of the gene for improving vitamin $B_6$ production.

In the verification process of the invention, we found a gene, named pdxR, which complements a vitamin $B_6$-deficient mutant of *S. meliloti* IFO 14782 (DSM 10226) that requires 4-hydroxy-L-threonine (referred to as 4-HT hereinafter) or vitamin $B_6$ for the growth. The pdxR does not have homology to any genes disclosed as being involved in vitamin $B_6$ biosynthesis of *E. coli*.

According to search of the genome database of *S. meliloti* strain 1021 [Galibert et al., Science 293:668-672 (2001)], deduced amino acid sequence of pdxR suggested that PdxR is one of oxidoreductases such as dehydrogenases, reductases and oxidases. But it is very difficult to predict its substrate for PdxR. The pdxR gene was found to complement not only a vitamin $B_6$-deficient mutant of *S. meliloti* IFO 14782 but also a $pdxB^-$ mutant of *E. coli* lacking an EN4P dehydrogenase. These findings indicate that PdxR is involved in 4-PHT pathway of vitamin $B_6$ biosynthesis in *S. meliloti* and pdxR encodes oxidoreductases catalyzing oxidation of EN4P to 2-keto-EN4P.

By further experiments, a gene product encoded by pdxR gene of *S. meliloti* in the present invention was found to contain FAD and to catalyze the oxidation of EN4P using an electron acceptor such as cytochrome c, 2,6-dichlorophenolindophenol (DCIP), or ferricyanide, but not such as $O_2$, $NAD^+$ or $NADP^+$. Evidence is presented that the pdxR gene product is a dehydrogenase with electron acceptors rather than an oxidase and completely different from EN4P dehydrogenase with $NAD^+$ of *E. coli*.

The present invention is directed to DNA sequence comprising a DNA sequence which encodes PdxR, which is an FAD-dependent EN4P dehydrogenase involved in vitamin $B_6$ synthesis, as disclosed in the sequence listing, as well as their complementary strands, or those which include these sequences, DNA sequences which hybridize, preferably under standard conditions, with such sequences or fragments thereof and DNA sequences, which because of the degeneration of the genetic code, do not hybridize under standard conditions with such sequences but which code for polypeptides having exactly the same amino acid sequence.

"Standard conditions" for hybridization mean in this context the conditions which are generally used by a person skilled in the art to detect specific hybridization signals, or preferably so called stringent hybridization and non-stringent washing conditions or more preferably so called moderately stringent conditions or even more preferably so called stringent hybridization and stringent washing conditions. For example, a condition is hybridizing in 2×SSC and 0.5% SDS at 45° C. for 1 hour and washing in 0.1×SSC and 0.5% SDS at 60° C. for 1 hour.

Present invention also includes DNA sequences that are at least 80% to 85%, preferably at least 86% to 90%, more preferably at least 91% to 95%, and particularly preferably more than 95% identical to the DNA sequence according to SEQ ID NO:1 or a fragment therefrom.

The present invention is also directed to polypeptides having FAD-dependent EN4P dehydrogenase activity, which are functional derivatives of the polypeptides of the present case. Such functional derivatives are defined on the basis of the amino acid sequences of the present invention by addition, insertion, deletion and/or substitution of one or more amino acid residues of such sequences, wherein such derivatives still have the activity of the FAD-dependent EN4P dehydrogenase. Such functional derivatives can be made either by chemical peptide synthesis known in the art or by recombinant means on the basis of the DNA sequence as disclosed herein by methods known in the state of the art. Amino acid exchanges in proteins and peptides which do not generally alter the activity of such molecules are known in the state of the art. The most commonly occurring exchanges are: Ala/ Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/ Ile, Leu/Val, Ala/Glu, Asp/Gly as well as these in reverse.

Furthermore, polypeptides according to the invention include a polypeptide according to SEQ ID NO: 2, in particular those with the activity of FAD-dependent EN4P dehydrogenase, and also those which are at least 80% to 85%, preferably at least 86% to 90%, more preferably at least 91% to 95%, and particularly preferably more than 95% identical to the polypeptide according to SEQ ID NO: 2 and have the activity mentioned.

To express the pdxR or the DNA sequence encoding FAD-dependent EN4P dehydrogenase efficiently, various promoters can be used; e.g., the original promoter existing upstream of the pdxR gene, promoter of antibiotic gene such as β-galactosidase of *E. coli* (lac), promoter of small ribosomal subunit of *S. meliloti* (pS1), trp-, tac-, trc-promoter, and any promoters which can be functional in the hosts consisting of microorganism including bacteria such as *E. coli* and *S. meliloti*.

For the object above, other regulatory elements such as a Shine-Dalgarno (SD) sequence (e.g., AGGAGG and so on, including natural and synthetic sequence operable in the host cell) and a transcriptional terminator (inverted repeat structure including any natural and synthetic sequences operable in the host cell) which are operable in the host cell into which the coding sequence will be introduced and used with the above described promoter.

A wide variety of host/cloning vector combinations may be employed in cloning the double-stranded DNA. Cloning vector is generally a plasmid or phage which contains a replication origin, regulatory elements, a cloning site including a multiple cloning site and selection markers such as antibiotic resistance genes including resistance genes for ampicillin, tetracycline, chloramphenicol, kanamycin, neomycin, streptomycin, gentamicin, spectinomycin etc (referred to as Ap, Tc, Cm, Km, Nm, Sm, Gm, Sp hereinafter, respectively).

Preferred vectors for the expression of the object gene in *E. coli* are selected from any vectors usually used in *E. coli*, such as pBR322 or its derivatives including pKK223-3, pUC18 and pBluescriptII, pACYC184 or its derivatives, and a vector derived from a broad host range plasmid such as RK2 and RSF1010. A preferred vector for the expression of the object gene in *S. meliloti* is selected from any vectors that can replicate in this microorganism, as well as in a preferred cloning organism such as *E. coli*. The preferred vector is a broad host range vector such as pVK100, pRK290, pLAFR1, and RSF1010 or a vector containing a replication origin functional in *S. meliloti* and another origin functional in *E. coli*.

To construct a host cell carrying an expression vector, various DNA transfer methods including transformation, transduction) and conjugal mating can be used. The method for constructing a transformed host cell may be selected from the methods well known in the field of molecular biology. Usual transformation and transduction systems can be used for *E. coli*. Conjugal mating system can be widely used in Gram-positive and Gram-negative bacteria including *E. coli* and *S. meliloti*.

Vitamin $B_6$-deficient mutant that has a mutated point on the pathway leading to 4-PHT can be constructed by transposon mutagenesis.

Transposon is a distinct DNA segment, which has a capacity to move into the genome. One of these transposons, Tn5, is a 5,818-bp composite transposon, consisting of two inverted repeats and three genes conferring resistance to the antibiotics. Tn5 has a low insertional specificity and Tn5 mutagenesis can be performed [Meade et al., J. Bacteriol. 149:114-122 (1982)]. A suicide vector, pSUP2021, which carries Tn5 derived from *Pseudomonas* and is not replicable in *S. meliloti*, can be used to introduce Tn5 insertion into the genome of *S. meliloti* [Simon et al., BIO/TECHNOLOGY 1:784 (1983)]. A helper plasmid, e.g., pRK2013 (ATCC 37159), which helps immobile plasmid transfer into other microorganism, can be used.

Tn5 on the suicide vector can be introduced into *S. meliloti* IFO 14782 by tri-parental conjugal mating in the following manner. *S. meliloti* as a recipient strain, *E. coli* harboring helper plasmid as a helper strain, and *E. coli* harboring donor plasmid as a donor strain are cultivated separately and mixed together. After mixed cultivation on plate, *S. meliloti* that has Tn5 integrated in its genome can be selected on agar plate containing appropriate antibiotics. Among these antibiotic-resistant mutants, mutants that produce vitamin $B_6$ less or none can be selected by the amount of vitamin $B_6$, which they produce, with vitamin $B_6$ detection plate. The less or none vitamin $B_6$ producing mutants can also be examined about requirement of intermediates on the pathway to vitamin $B_6$. With these supplement experiments, a mutated point on the pathway can be suggested.

A DNA segment, which complements vitamin $B_6$ deficient mutant, can be screened from genomic library of *S. meliloti*. Genomic library is comprised of large variety of partially digested chromosomal DNA ligated into cosmid and transferred to vitamin $B_6$ deficient mutant. Transconjugant complemented with target DNA segment can be obtained by growth on vitamin $B_6$-free plate. A DNA sequence of the segment can be determined by methods known in the state of the art.

PdxR is over-expressed to investigate a function of its product in host cell. When the PdxR is prepared to be over-expressed, the polymerase chain-reaction (PCR) method is suitable for adding restriction enzyme recognition site to place pdxR under control of a strong promoter. The primers for PCR are synthesized in accordance with the DNA sequence of pdxR and flanking region, and one primer contains restriction enzyme recognition sequence at its 5' end. The DNA fragment containing pdxR can be amplified by PCR using the primers and chromosomal DNA of *S. meliloti*. Amplified DNA can be ligated into a vector replicable in *E. coli* as described above in a desired structure. A plasmid, wherein amplified DNA is inserted, can be selected and the sequence of amplified region can be ascertained by methods known in the state of the art.

For preparation of the cell-free extract from the cells obtained by cultivation, general method such as sonication, cell breakage in the presence of glass beads or by French press homogenizer can be applied. If desired, treatment with a lytic enzyme such as lysozyme or zymolase at 15° C. to 45° C., preferably 20° C. to 40° C. for 1 to 3 hours can also be applied before the disruption in the above-mentioned way. For example, after centrifugation of culture broth, the resulting cells are washed with 0.85% (w/v) saline and suspended in a buffer such as Tris-HCl buffer, pH 7.5. After cell breakage, the resulting solution is centrifuged to separate the cell debris, and its supernatant can be used as cell-free extract.

The protein concentration was determined by the Lowry method.

EN4P dehydrogenase activity with an electron acceptor can be verified by observing or by measuring spectrophotometrically color change due to formation of reduced form from oxidized form of an electron acceptor such as cytochrome c, DCIP, or ferricyanide when EN4P dehydrogenase in this invention exist together with one of these electron acceptors in appropriate buffer.

The transformed host cell obtained in the present invention is incubated in a medium containing an assimilable carbon source, a digestible nitrogen source, an inorganic salt, and other nutrients necessary for their growth. As a carbon source, e.g., glucose, fructose, lactose, maltose, galactose, sucrose, starch, dextrin, or glycerol may be employed. As a nitrogen source, e.g., peptone, corn steep liquor, soybean powder, yeast extract, meat extract, ammonium chloride, ammonium sulfate, ammonium nitrate, urea, or their mixture thereof may be employed. Further, for trace elements, sulfates, hydrochlorides, or phosphates of calcium, magnesium, zinc, manganese, cobalt, and iron may be employed. If necessary, conventional nutrient factors, a trapping agent of phosphate ion, or an antifoaming agent, such as magnesium carbonate, aluminum oxide, allophane, animal oil, vegetable oil, or mineral oil can also be added supplementary in a fermentation medium. The pH of the culture medium may be about 5.0 to about 9.0, preferably about 6.5 to about 7.5. The cultivation temperature may be about 10° C. to about 40° C., preferably about 25° C. to about 35° C. The cultivation time may be about 1 day to about 15 days, preferably about 2 days to about 9 days. In the cultivation, aeration and agitation usually give favorable results.

After the cultivation, produced vitamin $B_6$ may also be separated from the culture broth and purified. For this purpose, a process generally used for extracting a certain product from the culture broth may be applied by utilizing various properties of vitamin $B_6$. Thus, e.g., the cells are removed from the culture broth, the desired substance in the supernatant is absorbed on active carbon, then eluted and purified further with an ion exchange resin. Alternatively, the culture filtrate is applied directly to an ion exchange resin and, after the elution, the desired product is recrystallized from mixture of alcohol and water.

A vitamin $B_6$ deficient mutant, *S. meliloti* 16C18, was obtained by screening of Tn5 insertion mutagenesis from *S. meliloti* IFO 14782 (DSM 10226). The mutant having a mutation point on 4-PHT pathway is necessary for isolation of pdxR gene encoding EN4P dehydrogenase and was deposited at the DSMZ (Deutsche Sammlung von Mikroorganismen und Zellkulturen GmbH) in Göttingen (Germany) on Sep. 17, 2002 under accession no. DSM15210 under the Budapest Treaty.

The invention is explained in more detail below with the aid of a few implementation examples. The following text is intended to indicate the materials and methods employed and to support the invention with experimental examples and comparative examples, but it is not construed as being limited thereto.

EXAMPLE 1

[A] Isolation of Vitamin $B_6$-Deficient Tn5 Insertion Mutant, *S. meliloti* 16C18

Vitamin $B_6$-deficient mutants were screened from Tn5 insertion mutants of *S. meliloti* IFO 14782 that is a natural high producer of vitamin $B_6$. Tn5 was introduced into *S. meliloti* IPO 14782 by tri-parental conjugal mating as described below. *S. meliloti* IFO 14782 as a recipient strain was inoculated in 5 ml of liquid LBMC medium consisting of 1% Tryptone Peptone (Becton Dickinson Microbiology systems, MD, USA), 0.5% Bacto Yeast Extract (Becton Dickinson Microbiology systems, MD, USA), 0.5% NaCl, 0.061% $MgSO_4.7H_2O$, and 0.036% $CaCl_2.2H_2O$ and incubated with shaking at 30° C. at 140 rpm for 16 hours. The culture (400 μl) was transferred into fresh medium and incubated for 6 hours again. *E. coli* HB101 harboring pRK2013 (ATCC 37159) as a helper strain was inoculated in 5 ml of liquid LB medium consisting of 1% Tryptone Peptone, 0.5% Bacto Yeast Extract, and 0.5% NaCl containing 50 μg/ml of Km and incubated with shaking at 37° C. at 140 rpm for 16 hours. The culture (100 μl) was transferred into fresh medium and incubated for 6 hours again. *E. coli* HB101 harboring pSUP2021 as a Tn5 donor strain was inoculated in 5 ml of liquid LB medium containing 50 μg/ml of Km and incubated with shaking at 37° C. at 140 rpm for 16 hours. The culture (100 μl) was transferred into fresh medium and incubated for 6 hours again. Each strain was harvested and cells were mixed at 1:1:4 (v/v/v) ratio. The mixture was put on a nitrocellulose filter placed on LBMC agar plate. After this plate was incubated for 20 hours at 30° C., cells on the filter were scratched and suspended in sterilized 0.85% saline. The suspension was diluted appropriately and spread on LBMC plates containing 20 μg/ml of Nal (to select for *S. meliloti* IFO 14782) and 50 μg/ml of Nm (to select for Tn5). After incubation of the plates at 30° C. for 4 days, about 10,000 colonies appeared on the plates. The frequency of Nm resistant colony was $4.2 \times 10^{-8}$/recipient.

These colonies were streaked on LBMC plates containing same antibiotics and incubated for 2 days at 30° C. The cells grown on the plates were inoculated on vitamin $B_6$ assay plates (Table 1) containing *Saccharomyces carlsbergensis* ATCC 9080 as a vitamin $B_6$ indicator strain. After incubation for 2 days at 30° C., one colony that had no halo of *Saccharomyces carlsbergensis* ATCC 9080 was obtained. The strain was named as *S. meliloti* 16C18. Strain 16C18 did not grow on EMM plate (Table 1), wherein parent strain, *S. meliloti* IFO 14782, grew. Further, *S. meliloti* 16C18 grew on EMM plate which was supplemented with 4 mg/L of 4-HT or 400 μg/L of PN. This result suggests that *S. meliloti* 16C18 is a vitamin $B_6$ deficient mutant possessing a mutation point on 4-PHT pathway.

TABLE 1

Media composition (vitamin $B_6$ assay plate and EMM plate)

| Ingredient | vitamin $B_6$ assay plate | EMM plate |
|---|---|---|
| glucose | 50 g | 10 g |
| vitamin free casamino acid | — | 8 g |
| L-arginine | 160 mg | — |
| L-aspartic acid | 20 mg | — |
| L-glutamic acid | 200 mg | — |
| glycine | 40 mg | — |
| L-histidine | 80 mg | — |
| L-isoleucine | 180 mg | — |
| L-leucine | 400 mg | — |
| L-lysine | 280 mg | — |
| L-methionine | 80 mg | — |
| L-phenylalanine | 160 mg | — |
| L-threonine | 160 mg | — |
| L-tyrosine | 80 mg | — |
| L-valine | 280 mg | — |
| $KH_2PO_4$ | 550 mg | — |
| $MnSO_4 \cdot 5H_2O$ | 2.5 mg | 2.5 mg |
| $MgSO_4 \cdot 7H_2O$ | 125 mg | 125 mg |

TABLE 1-continued

Media composition (vitamin $B_6$ assay plate and EMM plate)

| Ingredient | vitamin $B_6$ assay plate | EMM plate |
|---|---|---|
| $CaCl_2 \cdot 2H_2O$ | 125 mg | 125 mg |
| KCl | 425 g | 425 mg |
| $FeCl_3 \cdot 6H_2O$ | 2.5 mg | 250 µg |
| thiamin hydrochloride | 250 µg | 250 µg |
| biotin | 8 µg | 8 µg |
| deionized water | 1000 ml | 1000 ml |
| bacto-agar (Difco) | 15 g | 15 g |
| pH | 6.0 | 6.8 |

[B] Isolation of the DNA Fragment Complementing Growth of S. meliloti 16C18 on EMM Plate Genomic library of S. meliloti IFO 14782 was constructed as a tool to obtain DNA fragment which made S. meliloti 16C18 grow on EMM plate without 4-HT or PN.

Chromosomal DNA of S. meliloti IFO 14782 was prepared using QIAGEN Genomic-tips (QIAGEN, GmbH, Germany). The chromosomal DNA was digested with EcoRI. The partially digested DNA was subjected to agarose gel electrophoresis on 0.6% gel. A piece of gel containing 15-kb~35-kb DNA fragments was cut out and the DNA fragments were eluted from the gel by electrophoresis. Eluted DNA fragments were precipitated with ethanol and recovered by centrifugation. In parallel, 400 ng of plasmid pVK100 was completely digested with EcoRI and dephosphorylated with alkaline phosphatase. The treated pVK100 was ligated with above-mentioned chromosomal DNA fragments (1 µg) of S. meliloti IFO 14782 by ligation kit (Takara Bio Inc., Shiga, Japan). The DNA was subjected to in vitro packaging of phage (Amersham Biosciences Corp., NJ, USA). Then, E. coli ED8767 [Murray et al., Mol. Gen. Genet. 150:53-61 (1977)], which was harvested during exponential growth, was infected with the phage, which contains various DNA fragments of S. meliloti IFO 14782. The infected E. coli was spread out on LB medium containing 10 µg/ml of Tc. After incubation for 17 hours at 37° C., approximately 10,000 colonies appeared on plates. These colonies were scratched all together, incubated in LB liquid medium at 37° C. for 1 hour, dispensed into small tubes with lids, and stored at −120° C. This genomic library in E. coli ED8767 was introduced into S. meliloti 16C18 by tri-parental conjugal mating as described below to screen transconjugants, which grew EMM plate without PN.

S. meliloti 16C18 as a recipient strain was inoculated in liquid LBMC medium and incubated with shaking at 30° C. at 140 rpm for 16 hours. The culture (400 µl) was transferred into fresh same medium and incubated for 6 hours again. E. coli HB101 harboring pRK2013 as a helper strain was inoculated in liquid LB medium containing 50 µg/ml of Km and incubated with shaking at 37° C. at 140 rpm for 16 hours. The culture (100 µl) was transferred into fresh medium and incubated for 6 hours again. Frozen-stored E. coli ED8767 harboring genomic library of S. meliloti IFO 14782 as a donor strain was inoculated in liquid LB medium containing 10 µg/ml of Tc and incubated with shaking at 30° C. at 140 rpm for 2 hours. After each strain was harvested, they were mixed at 1:1:1 ratio and the mixed cells were put on nitrocellulose filter placed on LBMC agar plate. After incubation for 20 hours at 30° C., cells on the filter were scratched and suspended into sterile 0.85% saline. The suspension was diluted and spread out on EMM plates containing 20 µg/ml of Nal (to select for S. meliloti) and 10 µg/ml of Tc (to select for the plasmid). After incubation at 30° C. for 8 days, 4 colonies appeared. Plasmids in these colonies were prepared, digested with restriction enzymes, and analyzed on agarose gel. Among these plasmids, one plasmid, which has a 23.0-kb insertion, was designated as pSHT09. A 2.5-kb DNA fragment generated by cleaving pSHT09 with EcoRI was ligated into pVK100 that had been opened at EcoRI site and the ligation mixture was transformed to E. coli HB101 competent cells (Takara Bio Inc., Shiga, Japan). Plasmids in appeared colonies were prepared, digested with restriction enzymes and analyzed on agarose gel. A plasmid, which contains a 2.5-kb insertion, was named pVK-HTS1. This plasmid was transferred into S. meliloti 16C18 by tri-parental conjugal mating as described above. S. meliloti 16C18 harboring pVK-HTS1 (S. meliloti 16C18/pVK-HTS1) grew on EMM plate without PN or 4-HT. This indicates that there is a gene complementing the growth of S. meliloti 16C18 within the 2.5-kb DNA fragment.

[C] Specification of the Complementing Gene

DNA sequence of the 2.5-kb fragment, which was obtained in Example 1[B], was determined with an ALFred DNA sequencer (Amersham Biosciences Corp., NJ, USA). Within the sequence, there was an open reading frame (referred to as ORF hereafter) whose length was 1491-bp (SEQ ID NO: 1). Sequence of the ORF was identical with the CDS region of SMc00985 (951316-952806, complement) in accession number NC_003047. Deduced amino acid sequence of the CDS (SEQ ID NO: 2) was predicted as a putative oxidoreductase, though its substrate had not been identified. Then the ORF was named as pdxR. A recombinant plasmid, which carries the pdxR, was constructed as follows. The DNA fragment containing pdxR and flanking region was amplified from 100 ng of chromosomal DNA of S. meliloti IFO 14782 with advantage-HF PCR kit (Clontech Laboratories, Inc. CA, USA) using 10-pmol of two primers, SEQ ID NOs: 3 and 4. One primer for amino-terminal was designed to contain an initiation codon just after the EcoRI site. Reaction condition was as follows; after holding 15 sec at 94° C., 25 cycles of 15 sec at 94° C., 15 sec at 50° C., 3 min at 68° C. The resultant 2.2-kb PCR product was inserted into pCRII-TOPO vector with TOPO TA cloning kit (Invitrogen Japan K.K., Japan). It was ascertained that sequence of pdxR in amplified region was identical with the corresponding CDS region of SMc00985 (951316-952806, complement) in accession number NC_003047. The 1.7-kb fragment of DNA corresponding to the amplified region was cut out with EcoRI and the fragment was recovered from agarose gel with QIAEXII (QIAGEN, GmbH, Germany). The 1.7-kb fragment was ligated to pKK223-3 expression vector (Amersham Biosciences Corp., NJ, USA) that had been opened with EcoRI and dephosphorylated by alkaline phosphatase. After transformation of E. coli JM109 competent cells (Takara Bio. Inc., Shiga, Japan) with the ligation mixture, plasmids in transformants were prepared, digested with restriction enzyme and analyzed on agarose gel. A recombinant plasmid, pKK-pdxR, wherein pdxR gene was inserted into the EcoRI site of pKK223-3 and into the same direction of tac promoter on the vector, was obtained. Plasmid pKK-pdxR was prepared with E. coli JM109/pKK-pdxR with QIAGEN Midi kit (QIAGEN GmbH, Germany). Thus obtained plasmid pKK-pdxR was digested with BamH I. Resulting 2-kb fragment containing tac promoter and pdxR was purified from agarose gel. The 2-kb fragment was ligated to pVK100 that had been opened with Bgl II and dephosphorylated with alkaline phosphatase. E. coli HB101 competent cells (Takara Bio Inc., Shiga, Japan) were transformed with this ligation mixture and plasmids in transformants were prepared, digested with restriction enzyme and analyzed on agarose gel. A recombinant plasmid pVK-PdxR, wherein tac promoter and pdxR gene were inserted into the Bgl II site of pVK100 as the opposite direction of Km resistant gene, was obtained.

Thus obtained pVK-pdxR was introduced into *S. meliloti* 16C18 by tri-parental conjugal mating as described in Example 1[B] except selection plates, which are LBMC containing 20 mg/L of Nal and 10 mg/L of Tc. Transconjugants grown on selection plates were obtained and plasmids in the transconjugants were ascertained to have the same structure of pVK-pdxR. Then, these transconjugants were streaked on EMM plate containing 50 mg/L of Nm and 10 mg/L of Tc. After incubation at 30° C., all tested transconjugants could grow on the plate, on which *S. meliloti* 16C18/pVK100 could not grow. This indicates that the amplified pdxR placed under tac promoter can complement *S. meliloti* 16C18.

EXAMPLE 2

Enzyme Function and Characteristics of a PdxR Gene Product

[A] Complementation of *E. coli* PdxB⁻ Mutant by PdxR Gene

Thus obtained pKK-pdxR in Example 1[C] was transformed into *E. coli* WG1012, which is PdxB⁻ mutant (Dempsey, W. B., J. Bacteriol., vol. 100, p. 295, 1969). Resultant transformants and parent strain, *E. coli* WG1012, were streaked on EMM plates with and without PN. After incubation for 16 hours at 37° C., all tested transformants could grow on EMM plates without PN, on which *E. coli* WG1012 could not grow. This indicates that pdxR gene product of *S. meliloti* has the same function as pdxB gene product in *E. coli*, which converts EN4P to 2-keto-EN4P.

[B] Enzyme Reaction System for EN4P Oxidoreductase (1) Construction of Microorganisms for Production of PdxR Gene Product and Preparation of Cell-Free Extract Then *S. meliloti* 16C18 and one clone of the transconjugants obtained by introduction of pVK-pdxR into *S. meliloti* 16C18 as described in Example 1[C], *S. meliloti* 16C18/pVK-pdxR, were grown in tubes containing 6 ml of a seed medium composed of 1% glucose, 0.5% Polypepton (Nihon Pharmaceutical Co., Osaka, Japan), 0.2% Bacto Yeast Extract, 0.1% $KH_2PO_4$, 0.05% $MgSO_4.7H_2O$, 0.001% $MnSO_4.5H_2O$, and 0.001% $FeSO_4.7H_2O$ at 28° C. for 17 hours.

The seed cultures (each 4 ml) were transferred into 500-ml flasks containing 200 ml of a fermentation medium composed of 4% glucose, 4% Polypepton S (Nihon Pharmaceutical Co., Osaka, Japan), 0.8% Bacto Yeast Extract, 0.05% $MgSO_4.7H_2O$, 0.05% $MnSO_4.5H_2O$, 0.001% $FeSO_4.7H_2O$, and one drop of Actocol (Takeda Chemical Industries, Ltd., Osaka, Japan). The flasks were shaken on a rotary shaker (180 rpm) at 28° C. After cultivation for 72 hours, 35.3 and 35.5 g of wet cells were obtained from 2 liters of the culture broth of *S. meliloti* 16C18 and *S. meliloti* 16C18/pVK-pdxR, respectively, by centrifugation at 10,400×g for 10 minutes, and the cells were washed with 200 ml of 0.85% NaCl solution twice and stored at −30° C. until use.

The frozen cells were thawed slowly, suspended with 200 ml of 10 mM Tris-HCl buffer, pH 7.5. The suspension was passed through a French pressure cell at 800 kg/cm². The homogenate was centrifuged to remove the cell debris at 37,000×g for 90 minutes and then each 165 ml of supernatants was used as cell-free extract (CFE) and the protein contents in *S. meliloti* 16C18 and *S. meliloti* 16C18/pVK-pdxR were 5,030 and 5,042 mg, respectively.

To confirm the expression of PdxR, the each CFE (5 ml) was dialyzed overnight against 4 liters of 10 mM Tris-HCl buffer, pH 7.5, and subjected to SDS-PAGE on 10% (w/v) gels and stained with Coomassie Brilliant Blue (Rapid Stain CBB Kit, nacalai tesque Japan). Overexpression of polypeptide with an expected molecular size (53.0 kDa) was detected in *S. meliloti* 16C18/pVK-pdxR but not in *S. meliloti* 16C18. Therefore, the CFEs were used for further study.

(2) EN4P Oxidoreductase Activities of Cell-Free Extract

EN4P was prepared from E4P (Sigma Chemical Co., St. Louis, Mo., USA) by the bromine oxidation according to the method of Horecker [Methods in Enzymology 3:172-174 (1957)]. The product was confirmed as m/z 215 (M−H)⁻ by negative fast atom bombardment-mass spectrometric analysis (a Jeol SX-102/102 mass spectrometer) and chromatographic properties of the product was identical with those of material prepared by the method of Zhao et al. [J. Bacteriol. 177:2804-2812 (1995)].

Enzyme reaction system for PdxR was studied using CFE prepared in Example 2[B] (1). EN4P oxidase activity with oxygen in CFE was examined by observation of color change (from colorless to pinkish) due to formation of hydrogen peroxide by a modification of 4-aminoantipyrine peroxidase system used for sarcosine oxidase assay by Inouye et al. as follows. Reaction mixture (150 µl) contained 50 mM potassium phosphate buffer, pH 7.0, 2.3 mM EN4P, 0.47 mM 4-aminoantipyrine (Wako Pure chemical Industries, Ltd., Osaka, Japan), 2 mM phenol (Wako Pure chemical Industries, Ltd., Osaka, Japan), 19 U horseradish peroxidase (Sigma Chemical Co.), and CFE (0.16 mg protein), and color changes of reaction mixtures were observed at room temperature (21° C.) or at 37° C. But, after 10 min, no color change occurred at the both temperatures in the reaction mixtures with CFE prepared from cells of *S. meliloti* 16C18 or *S. meliloti* 16C18/pVK-pdxR, whereas hydrogen peroxide standard solutions gave pinkish colors with intensity corresponding to the concentrations. From the results, the both CFEs were determined to have no EN4P oxidase activity with oxygen.

EN4P dehydrogenase activity with NAD⁺ or NADP⁺ in CFE was determined by the formation of NADH or NADPH, which absorbs at 340 nm. Reaction mixture (150 µl) for assaying EN4P dehydrogenase activity contained 33 mM potassium phosphate buffer, pH 7.0, 2.3 mM EN4P, 1 mM NAD⁺ or NADP⁺, and CFE prepared from cells of *S. meliloti* 16C18 or *S. meliloti* 16C18/pVK-pdxR (each 0.16 mg protein). The increase of $A_{340}$ was monitored at room temperature (21° C.) for 1 min in a UV-VIS recording spectrophotometer UV 2200 (Shimadzu Instruments, Inc., Kyoto, Japan), but the increase of $A_{340}$ was not observed in enzyme reaction mixtures with any CFEs. Therefore, the both CFEs were determined to have no NAD⁺ or NADP⁺ dependent EN4P dehydrogenase activity. EN4P dehydrogenase activity with an electron acceptor in CFE was examined at room temperature (21° C.) by color change due to formation of reduced form from oxidized form of an electron acceptor. Reaction mixture (150 µl) contained 33 mM potassium phosphate buffer, pH 7.0, 2.3 mM EN4P, CFE (0.16 mg protein), and an electron acceptor such as 2,6-dichlorophenolindophenol (0.091 mM) (Wako Pure chemical Industries, Ltd., Osaka, Japan) (referred to as DCIP hereinafter) or ferricyanide (1.3 mM) (Wako Pure chemical Industries, Ltd., Osaka, Japan). Discoloration of DCIP and ferricyanide occurred within 30 seconds and 1 minute respectively only when CFE prepared from cells of *S. meliloti* 16C18/pVK-pdxR was used in enzyme reaction system containing EN4P, although the discoloration of both electron acceptors never occurred in enzyme reaction system without EN4P in the presence of CFE of *S. meliloti* 16C18/pVK-pdxR or in enzyme reaction system with and without EN4P in the presence of CFE of *S. meliloti* 16C18 (Table 2). These results indicate that a pdxR gene product oxidizes EN4P with electron acceptor such as DCIP or ferricyanide.

TABLE 2

Color change of electron acceptors in reaction mixture

| | S. meliloti 16C18 | S. meliloti 16C18/pVK-pdxR |
|---|---|---|
| DCIP[1)] + EN4P[2)] | No change | Discoloration within 30 sec. |
| DCIP − EN4P | No change | No change |
| ferricyanide + EN4P | No change | Discoloration within 1 min. |
| ferricyanide − EN4P | No change | No change |

DCIP[1)]: 2,6-dichlorophenolindophenol,
EN4P[2)]: D-erythronate 4-phosphate.

Furthermore, possibility of cytochrome c instead of DCIP or ferricyanide in above-mentioned enzyme reaction system of EN4P dehydrogenase with an electron acceptor was examined by measuring change of absorption spectra in 400-600 nm spectral regions due to formation of reduced form from oxidized form of cytochrome c at room temperature (21° C.). Reaction mixture (150 µl) contained 33 mM potassium phosphate buffer, pH 7.0, 2.3 mM EN4P, 80 µM oxidized form of cytochrome c (from equine heart, Sigma Chemical Co.) as an electron acceptor, and CPE (0.16 mg protein). Absorption spectra of the reaction mixture of zero time and after 2, 5, 10, 15 and 20 min at room temperature (21° C.) were monitored with a UV-VIS recording spectrophotometer UV 2200. The absorption spectrum of zero time had only a broad peak at 525 nm, but spectra after 2 min appeared a new peak at 550 nm corresponding to reduced form of cytochrome c, and the absorption in the 550 nm region after 5, 10, 15 and 20 min was increased with time course. This result indicates that cytochrome c also works as electron acceptor in enzyme reaction system of EN4P dehydrogenase.

[C] Properties of EN4P Dehydrogenase (1) Purification of EN4P Dehydrogenase with Electron Acceptors The pdxR gene product having EN4P dehydrogenase activity with electron acceptors in CFE was purified by the following chromatography.

(Q Sepharose HP Chromatography)

The CFE (3,055 mg proteins) of *S. meliloti* 16C18/pVK-pdxR obtained in Example 2[B] (1) was applied to a Q sepharose HP column (44 mm in diameter and 12.5 cm in height; Amersham Pharmacia Biotech, Uppsala, Sweden), which was equilibrated with 10 mM Tris-HCl buffer, pH 7.5. After washing with 100 ml of 10 mM Tris-HCl buffer, pH 7.5, containing 0.1 M KCl, it was chromatographed with a linear gradient of KCl 0.1 to 0.4 M (total volume, 800 ml). After a small portion of each fractionated effluent was dialyzed overnight against of 10 mM Tris-HCl buffer, pH 7.5, enzyme activity was monitored by measuring the decrease in absorbance at 600 nm at room temperature (21° C.) due to the formation of reduced DCIP. Assay mixtures (150 µl) contained 33 mM potassium phosphate buffer, pH 7.0, 2.3 mM EN4P, 0.091 mM DCIP, and 2 µl of dialyzed samples. The active fraction was eluted at the concentration of 0.37 M KCl, collected and dialyzed overnight against 10 mM Tris-HCl buffer, pH 7.5.

(Resource Q Chromatography)

The dialyzed active fraction (58 mg proteins) obtained in Q sepharose HP chromatography was chromatographed with a Resource Q column 6 ml column (Amersham Pharmacia Biotech, Uppsala, Sweden), which was equilibrated with 10 mM Tris-HCl buffer, pH 7.5. After washing with 70 ml of 10 mM Tris-HCl buffer, pH 7.5, containing 0.1 M KCl, it was chromatographed with a linear gradient of KCl 0.1 to 0.4 M (total volume, 120 ml). After dialysis of each effluent against 10 mM Tris-HCl buffer, pH 7.5, enzyme activity was measured by the same method described in Q sepharose HP chromatography. The active fraction was eluted at the concentration of 0.22 M KCl, collected and dialyzed overnight against 10 mM Tris-HCl buffer, pH 7.5.

(HiPrep 16/60 Sephacryl S-200HR Chromatography)

The dialyzed sample from the previous step was concentrated by ultrafiltration (Centriplus YM-10 and followed by Microcon YM-10 concentrators, Amicon Inc., Beverly, Mass., USA) to 300 µl. The sample (21.6 mg proteins) was applied to a HiPrep 16/60 sephacryl S-200HR column (16 mm in diameter and 60 cm in height; Amersham Pharmacia Biotech, Uppsala, Sweden), which was equilibrated with 50 mM Tris-HCl buffer, pH 7.5, containing 150 mM KCl. After dialysis-of each effluent against 10 mM Tris-HCl buffer, pH 7.5, enzyme activity was measured by the same method described in Q sepharose HP chromatography. The active fraction was subjected to SDS-PAGE on 10% (w/v) gels and stained with Coomassie Brilliant Blue. The analysis indicated that the active fraction was almost homogeneous and had a polypeptide with a molecular weight of 53 kDa, which coincided with the molecular weight of the gene product deduced from a DNA sequence of pdxR.

(2) Characterization of Flavin Binding to PdxR Protein

To characterize a flavin binding to PdxR protein, ammonium sulfate fractionation was applied in the finally purified enzyme solution prepared in Example 2[C] (1) according to a method of Cammack [Biochem. J. 109:45-46 (1968)]. The enzyme solution (1 ml, containing 4.74 mg proteins) was dialyzed overnight against 1 liter of 80% (w/v) ammonium sulfate solution and its resultant precipitate in a dialysis membrane was collected by centrifugation at 34,800×g for 30 min, dissolved in 0.5 ml of 10 mM Tris-HCl, pH 7.5, and dialyzed overnight against 4 liters of the same buffer. The volume of dialyzed enzyme solution was brought to 1 ml with 10 mM Tris-HCl, pH 7.5.

Discoloration of DCIP in the enzyme reaction mixture containing 33 mM potassium phosphate buffer, pH 7.0, 2.3 mM EN4P, purified PdxR treated with ammonium sulfate (2.37 µg proteins), 0.091 mM 2,6-dichlorophenolindophenol, and flavin mononucleotide (FMN) (Sigma Chemical Co.) or FAD (Sigma Chemical Co.) with various concentrations was observed at room temperature (21° C.). The degree of discoloration was judged at 3 minutes.

From the test, discoloration of DCIP occurred in reaction mixtures with FAD concentrations greater than 0.014 µM, but did not occur in those without flavin and with any FMN concentrations as shown in Table 3. These results indicate that FAD is a coenzyme of EN4P dehydrogenase, PdxR, of *S. meliloti*.

TABLE 3

Effect of flavin on discoloration of DCIP in reaction mixture

| | Discoloration degree | |
|---|---|---|
| Final conc. (μM) | FAD | FMN |
| 0 | − | − |
| 0.014 | + | − |
| 0.059 | ++ | − |
| 0.24 | +++ | − |
| 0.95 | ++++ | − |
| 0.38 | +++++ | − |
| 15.2 | +++++ | − |
| 61 | +++++ | − |

(3) Substrate Specificity of PdxR

Substrate specificity of PdxR was examined using the finally purified enzyme solution prepared in Example 2[C] (1). The standard enzyme assay was performed as follows: the basal reaction mixture (total volume 150 μl) consisting of 33 mM potassium phosphate buffer (pH 7.0), 2.4 μg proteins, 0.091 mM DCIP, and water up to a total volume of 144 μl, and was incubated at room temperature (21° C.). Then, 6 μl of 57 mM substrates solution listed in Table 4 was added to give a final concentration of 2.28 mM, and the whole was incubated at room temperature. The decrease in $A_{600}$ was monitored at 21° C. for 1 minute for EN4P dehydrogenase read with a UV-VIS recording spectrophotometer UV 2200. One unit of the enzyme activity was defined as the amount of enzyme reduced 1 nmol of DCIP for 1 minute under the action of EN4P dehydrogenase in the assay system described above. From the test, PdxR oxidized only EN4P, and did not oxidize other α-hydroxy acids tested.

TABLE 4

Substrate specificity of PdxR

| Substrates | Activity (nmol/min/mg protein) |
|---|---|
| None | 0 |
| EN4P | 946 |
| glycolate | 0 |
| glyoxylate | 0 |
| D(+) glyceric acid | 0 |
| L-(+)-lactic acid | 0 |
| D,L-lactate | 0 |
| D,L-isocitrate | 0 |
| L-malic acid | 0 |
| D-erythronate | 0 |
| glycolic acid 2-phosphate | 0 |
| D-(−)-glyceric acid 3-phosphate | 0 |

EXAMPLE 3

Production of Vitamin $B_6$ by Recombinant S. meliloti pVK-pdxR obtained in Example 1[C] was introduced into S. meliloti IFO 14782 by tri-parental conjugal mating as described in Example 1[C]. Transconjugants grown on LBMC containing 20 mg/l of Nal and 10 mg/L of Tc were obtained. Plasmids in the transconjugants were ascertained to have the same structure of pVK-pdxR. Thus obtained S. meliloti IFO 14782/pVK-pdxR and the parent strain, S. meliloti IFO 14782, were incubated on a LBMC agar plate at 30° C. for 48 hours, and a loopful of each strain was inoculated to tubes containing 8 ml of a seed medium composed of 1% glucose, 1% corn steep liquor (Nihon Syokuhin Kako Co., Ltd., Tokyo, Japan), 0.2% Bacto Yeast Extract, 0.05% $MgSO_4.7H_2O$, 0.001% $MnSO_4.5H_2O$, and 0.001% $FeSO_4.7H_2O$, pH 7.0, and then the tubes were shaken on a reciprocal shaker at 275 rpm at 30° C.

After shaking for 17 hours, each 4 ml of culture broth was transferred to 500-ml flasks with two baffles containing 200 ml of a production medium composed of 6% glucose, 4% corn steep liquor, 0.8% Bacto Yeast Extract, 0.05% $MgSO_4.7H_2O$, 0.05% $MnSO_4.5H_2O$, 1% Allophosite (Shinagawa Chemicals Co., Ltd., Tokyo, Japan), and 0.025% Actocol, pH 6.8, and shaken on a rotary shaker at 180 rpm at 30° C.

After cultivation for 7 days, contents of vitamin $B_6$ in the supernatant of each culture broth were quantified by high pressure liquid chromatography (referred to as HPLC hereinafter) and produced vitamin $B_6$ was calculated by the internal standard method with 4'-deoxypyridoxol as described below. To prepare the samples for HPLC, 200 μl of 500 mg/l of 4'-deoxypyridoxol as internal substance, 50 μl of 60% perchloric acid, and 500 μl of water were mixed with 500 μl of the standard solutions of pyridoxol (0-100 mg/L) or of the supernatant from the culture broth. Then the mixture was put on ice for 10 min. After centrifugation at 18,000×g for 10 min, a portion of the mixture was loaded on the following column. The analytical conditions were as follows: column, Capcell pak C18 SG120 (4.6×250 mm) (Shiseido Co., Ltd., Tokyo, Japan); mobile phase, 0.1 M sodium perchlorate, 0.1 M potassium phosphate, and 2% acetonitrile (pH 3.5); column temperature, 25-26° C.; flow rate, 1.0 ml/min; and detector, ultraviolet (UV) (at 292 nm). As a result, S. meliloti IFO 14782/pVK-pdxR produced 76 mg of pyridoxol per liter and was about 1.2 times higher than the parent, S. meliloti IFO 14782 (Table 5).

TABLE 5

Pyridoxol productivities of S. meliloti IFO 14782 and S. meliloti IFO 14782/pVK-pdxR

| Microorganism | Pyridoxol (mg/L) | Magnitude of increasing |
|---|---|---|
| S. meliloti IFO 14782 (DSM 10226) | 63 | 1.0 |
| S. meliloti IFO 14782/pVK-pdxR | 76 | 1.2 |

EXAMPLE 4

Separation of Vitamin $B_6$ from Cultural Broth

Produced vitamin $B_6$ was recovered from the culture broth of S. meliloti IFO 14782/pVK-pdxR prepared in the same cultural conditions as described in Example 3. Pyridoxol at each purification step and the concentration was followed by HPLC as described in Example 3.

Two liters of the 168-hour culture broth containing 74 mg/L of vitamin $B_6$ was centrifuged at 7,500 rpm for 10 min. The pH of the resultant supernatant was adjusted to 3.1 with 1N HCl, and then the supernatant was applied to a column (5.5×15 cm) packed with 350 ml of Amberlite CG 120 ($H^+$ form, 100-200 mesh, Rohm and Haas Company, Philadelphia, Pa., USA). The column was washed with 500 ml of deionized water and then eluted with 5% ammonium hydroxide. The vitamin $B_6$ fractions were concentrated under reduced pressure. The residue thus obtained was dissolved in 10 ml of deionized water, and the solution was charged on a column (5.5×16 cm) packed with 380 ml of Dowex 1×4 ($OH^−$ form, 200-400 mesh, Dow Chemical Co., Ltd., Midland, Mich., USA), and then washed with 500 ml of deionized water. The column was then eluted with 0.1 N HCl. The fractions containing pyridoxol were concentrated to small volume under reduced pressure. After the solid residue was dissolved in small amount of hot ethanol, the solution was kept standing at 4° C. overnight. The resultant precipitates were collected by filtration and dried in vacuum to obtain 119 mg of crude crystals. It was recrystallized from ethanol to obtain 91.6 mg of white crystals having a melting point of 160° C. The infrared absorption, UV absorption, and NMR spectrum of the product of the product coincided with those of authentic pyridoxol.

---

The invention claimed is:

1. A process for the biological production of vitamin B6 which comprises cultivating a host cell transformed or transfected by an isolated DNA or by a vector or plasmid comprising the isolated DNA under conditions conducive to the production of vitamin B6, and recovering vitamin B6 from the culture, wherein the host cell is selected from *Sinorhizobium* or *Escherichia* and wherein the isolated DNA comprises a nucleotide sequence encoding PdxR, which is a flavin adenine dinucleotide-dependent D-erythronate 4-phosphate dehydrogenase, selected from the group consisting of:
   (a) a DNA sequence of SEQ ID NO:1;
   (b) a DNA sequence encoding a polypeptide which is at least 95% identical to SEQ ID NO: 2, and encodes a polypeptide having the activity of flavin adenine dinucleotide-dependent D-erythronate 4-phosphate dehydrogenase; and
   (c) a DNA sequence encoding a polypeptide which comprises the amino acid sequence of SEQ ID NO: 2, and encodes a polypeptide having the activity of flavin adenine dinucleotide-dependent D-erythronate 4-phosphate dehydrogenase.

2. A process for the biological production of vitamin $B_6$ which comprises introducing the isolated DNA as claimed in any one of (a) to (c) in claim 1 into an appropriate host cell selected from *Sinorhizobium meliloti* or *Escherichia coli*, cultivating the obtained host cell under conditions conducive to the production of vitamin $B_6$, and recovering vitamin $B_6$ from the culture.

3. The process according to claim 1, wherein said host cell belongs to the genus *Sinorhizobium*.

* * * * *

SEQUENCE LISTING

<160> NUMBER OF SEQ ID NOS: 4

<210> SEQ ID NO 1
<211> LENGTH: 1491
<212> TYPE: DNA
<213> ORGANISM: Sinorhizobium meliloti

<400> SEQUENCE: 1

```
atggccatcg gcacgcttga agcaaccacg ttgatccgag gcagggccat gaccaccgta      60
cttccttctc ccgaactcat cgcctccttc gtcgatatcg tcgggcctgg caatgccctc     120
accgcacccg ccgacacggc accctacctc gtcgagtccc gcgggctcta ccgcggcacg     180
acgccgctcg tgctcaggcc cggctccgtc gaggaagttt cgctggtgat gcggcttgcg     240
agtcagaccc gaacggcagt cgtgccgcag gcggcaata ccggacatgt ggccggacag     300
attccacgcg agggcaaagc cgacgtggtc ctttccctcg agcggctgaa ccgcatccgc     360
gacatcgacc cggtcggcaa cgtgatcgtg gccgacgccg gctgtatcct ggcggacatc     420
cagaaggccg ccgatgacgt cgaccggctt tttccctgt cactcggctc ggaaggctct     480
gcccggatcg gcggcaatct ttcgaccaat gccggcggca ctgccgtgct tgcctatggg     540
aacatgcgcc agctctgcct ggggctggaa gtcgtgctcc cgaccgggga gatctgggat     600
gggctcagac gcctcaggaa ggacaatacc ggctacgatc tgcgcgatct tttcatcggc     660
gccgagggaa cgctcggcgt cataaccggc gccgttttga agctctttcc gaaaccgcgc     720
ggccaccagg tggcctttgc cggcctcagg agcgtcgagg acgcacttac gcttttcgat     780
cgggcaacaa gcgtctgcgg gccggccctg acgggcttcg aactgatgcc gcggctcggc     840
atcgagttca ccacccggca catcgccggc gtcagagatc cgatggaaac gacgcatccg     900
tggtacgcgc tgatcgatat ctccacctcg gataccgccg aaagcgcgga acggatggtg     960
caagaccttc tcgaagccgt cattgccgac ggtctcgtcg aaaacgcggt catcgcccag    1020
aacgaagcgc aacgcagagc gctctggcac atgcgagaaa gcatgtcgcc ggcacaaaag    1080
cctgagggtg gctccatcaa gcatgacgtt tcggtcccgg tgtcgagcat tcggccttc    1140 atgacggagg cggatgcgct ggtctccaag gccatccccg gcgcgcgcat ctgcgccttc    1200
ggccatatgg gcgacggcaa tatccactac aacatctccc agcccgtcgg cgcggacaag    1260
cagagctttc tcgatcggtg gcgcgagatc aatgcgatcg ttcacgccgt cgtgctcaaa    1320
catgacggct cgatctctgc cgagcatggc atcgccagt tgaagcgaga cgaactcgcg    1380
gcgatccgct cgccgatcga gatcgagctc atgcgacgga tcaagcacgc cttcgacccg    1440
gcggggatca tgaaccccga taaggtgctg cgcgaggatc gaggcgagta a            1491
```

<210> SEQ ID NO 2
<211> LENGTH: 496
<212> TYPE: PRT
<213> ORGANISM: Sinorhizobium meliloti

<400> SEQUENCE: 2

-continued

```
Met Ala Ile Gly Thr Leu Glu Ala Thr Thr Leu Ile Arg Gly Arg Ala
                 5                  10                  15
Met Thr Thr Val Leu Pro Ser Pro Glu Leu Ile Ala Ser Phe Val Asp
             20                  25                  30
Ile Val Gly Pro Gly Asn Ala Leu Thr Ala Pro Ala Asp Thr Ala Pro
         35                  40                  45
Tyr Leu Val Glu Ser Arg Gly Leu Tyr Arg Gly Thr Thr Pro Leu Val
     50                  55                  60
Leu Arg Pro Gly Ser Val Glu Val Ser Leu Val Met Arg Leu Ala
 65                  70                  75                  80
Ser Gln Thr Arg Thr Ala Val Val Pro Gln Gly Gly Asn Thr Gly His
                 85                  90                  95
Val Ala Gly Gln Ile Pro Arg Glu Gly Lys Ala Asp Val Val Leu Ser
             100                 105                 110
Leu Glu Arg Leu Asn Arg Ile Arg Asp Ile Asp Pro Val Gly Asn Val
         115                 120                 125
Ile Val Ala Asp Ala Gly Cys Ile Leu Ala Asp Ile Gln Lys Ala Ala
     130                 135                 140
Asp Asp Val Asp Arg Leu Phe Pro Leu Ser Leu Gly Ser Glu Gly Ser
145                 150                 155                 160
Ala Arg Ile Gly Gly Asn Leu Ser Thr Asn Ala Gly Gly Thr Ala Val
                 165                 170                 175
Leu Ala Tyr Gly Asn Met Arg Gln Leu Cys Leu Gly Leu Glu Val Val
             180                 185                 190
Leu Pro Thr Gly Glu Ile Trp Asp Gly Leu Arg Arg Leu Arg Lys Asp
         195                 200                 205
Asn Thr Gly Tyr Asp Leu Arg Asp Leu Phe Ile Gly Ala Glu Gly Thr
     210                 215                 220
Leu Gly Val Ile Thr Gly Ala Val Leu Lys Leu Phe Pro Lys Pro Arg
225                 230                 235                 240
Gly His Gln Val Ala Phe Ala Gly Leu Arg Ser Val Glu Asp Ala Leu
                 245                 250                 255
Thr Leu Phe Asp Arg Ala Thr Ser Val Cys Gly Pro Ala Leu Thr Gly
             260                 265                 270
Phe Glu Leu Met Pro Arg Leu Gly Ile Glu Phe Thr Thr Arg His Ile
         275                 280                 285
Ala Gly Val Arg Asp Pro Met Glu Thr Thr His Pro Trp Tyr Ala Leu
     290                 295                 300
Ile Asp Ile Ser Thr Ser Asp Thr Ala Glu Ser Ala Glu Arg Met Val
305                 310                 315                 320
Gln Asp Leu Leu Glu Ala Val Ile Ala Asp Gly Leu Val Glu Asn Ala
                 325                 330                 335
Val Ile Ala Gln Asn Glu Ala Gln Arg Arg Ala Leu Trp His Met Arg
             340                 345                 350
Glu Ser Met Ser Pro Ala Gln Lys Pro Glu Gly Gly Ser Ile Lys His
         355                 360                 365
Asp Val Ser Val Pro Val Ser Ser Ile Pro Ala Phe Met Thr Glu Ala
     370                 375                 380
Asp Ala Leu Val Ser Lys Ala Ile Pro Gly Ala Arg Ile Cys Ala Phe
385                 390                 395                 400
Gly His Met Gly Asp Gly Asn Ile His Tyr Asn Ile Ser Gln Pro Val
                 405                 410                 415
Gly Ala Asp Lys Gln Ser Phe Leu Asp Arg Trp Arg Glu Ile Asn Ala
```

-continued

```
                    420                 425                 430
Ile Val His Ala Val Val Leu Lys His Asp Gly Ser Ile Ser Ala Glu
        435                 440                 445

His Gly Ile Gly Gln Leu Lys Arg Asp Glu Leu Ala Ala Ile Arg Ser
    450                 455                 460

Pro Ile Glu Ile Glu Leu Met Arg Arg Ile Lys His Ala Phe Asp Pro
465                 470                 475                 480

Ala Gly Ile Met Asn Pro Asp Lys Val Leu Arg Glu Asp Arg Gly Glu
                485                 490                 495

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 3
gaattcatgg ccatcggca                                          19

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 4
ccacttccct tgtagtacga gct                                     23
```